United States Patent
Nappa et al.

(10) Patent No.: US 7,129,383 B2
(45) Date of Patent: Oct. 31, 2006

(54) PROCESSES FOR THE PREPARATION OF 2-CHLORO-1,1,1,2,3,3,3-HEPTAFLUORO-PROPANE, HEXAFLUOROPROPENE AND 1,1,1,2,3,3,3-HEPTAFLUOROPROPANE

(75) Inventors: Mario J. Nappa, Newark, DE (US); Velliyur Nott Mallikarjuna Rao, Wilmington, DE (US); H. David Rosenfeld, Drumore, PA (US); Sekhar Subramoney, Hockessin, DE (US); Munirpallam A. Subramanian, Kennett Square, PA (US); Allen C. Sievert, Elkton, MD (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 28 days.

(21) Appl. No.: 10/523,223

(22) PCT Filed: Aug. 21, 2003

(86) PCT No.: PCT/US03/26331

§ 371 (c)(1),
(2), (4) Date: Jan. 31, 2005

(87) PCT Pub. No.: WO2004/018397

PCT Pub. Date: Mar. 4, 2004

(65) Prior Publication Data

US 2005/0222471 A1 Oct. 6, 2005

Related U.S. Application Data

(60) Provisional application No. 60/405,222, filed on Aug. 22, 2002.

(30) Foreign Application Priority Data

Aug. 22, 2002 (US) ................. 60/405,222

(51) Int. Cl.
C07C 17/00 (2006.01)
C07C 17/266 (2006.01)
C07C 17/10 (2006.01)

(52) U.S. Cl. ............. 570/169; 164/166; 164/172; 164/176

(58) Field of Classification Search .......... 570/169, 570/164, 166, 172, 176
See application file for complete search history.

(56) References Cited

U.S. PATENT DOCUMENTS

| 3,865,885 A | 2/1975 | Bruce, Jr. |
| 3,878,257 A | 4/1975 | Bruce, Jr. |
| 4,843,181 A | 6/1989 | Gumprecht et al. |
| 5,043,491 A | 8/1991 | Webster et al. |
| 5,057,634 A | 10/1991 | Webster et al. |
| 5,068,472 A | 11/1991 | Webster et al. |
| 5,364,992 A | 11/1994 | Manogue et al. |
| 6,018,083 A | 1/2000 | Manogue et al. |

FOREIGN PATENT DOCUMENTS

| AU | A-29972/92 | 6/1993 |
| AU | A-80340/94 | 6/1995 |
| EP | 0 002 098 | 8/1981 |
| EP | 0 434 409 A | 6/1991 |
| GB | 902590 | 8/1962 |
| WO | WO 99/51553 A | 10/1999 |
| WO | WO 99/51555 | 10/1999 |
| WO | WO 2004/018093 A2 | 3/2004 |
| WO | WO 2004/018095 A1 | 3/2004 |

OTHER PUBLICATIONS

U.S. Appl. No. 10/523,226, pending.
U.S. Appl. No. 10/523,228, pending.

*Primary Examiner*—J. Parsa

(57) ABSTRACT

A process for the preparation of 2-chloro-1,1,1,3,3,3-heptafluoropropane is disclosed which involves (a) contacting a mixture comprising hydrogen fluoride, chlorine, and at least one starting material selected from the group consisting of halopropenes of the formula $CX_3CCl=CX_2$ and halopropanes of the formula the $CX_3CCIYCX_3$, wherein each X is independently F or Cl, and Y is H, Cl or F (provided that the number of X and Y which are F totals no more than six) with a chlorofluorination catalyst in a reaction zone to produce a product mixture comprising $CF_3CCIFCF_3$, HCl, HF, and underfluorinated halogenated hydrocarbon intermediates. The process is characterized by said chlorofluorination catalyst comprising at least one chromium-containing component selected from (i) a crystalline alpha-chromium oxide where at least 0.05 atom % of the chromium atoms in the alpha-chromium oxide lattice are replaced by nickel, trivalent cobalt or both nickel and trivalent cobalt, provided that no more than 2 atom % of the chromium atoms in the alpha-chromium oxide lattice are replaced by nickel and that the total amount of chromium atoms in the alpha-chromium oxide lattice that are replaced by nickel and trivalent cobalt is no more than 6 atom %, and (ii) a fluorinated crystalline oxide of (i). Also disclosed is a process for the manufacture of a mixture of HFC-227ea and hexafluoropropene by reacting a starting mixture comprising CFC-217ba and hydrogen in the vapor phase at an elevated temperature, optionally in the presence of a hydrogenation catalyst. This process involves preparing the CFC-217ba by the process described above.

3 Claims, No Drawings

PROCESSES FOR THE PREPARATION OF 2-CHLORO-1,1,1,2,3,3,3-HEPTAFLUORO-PROPANE, HEXAFLUOROPROPENE AND 1,1,1,2,3,3,3-HEPTAFLUOROPROPANE

This application represents a national filing under 35 USC 371 of International Application No. PCT/US03/026331 filed Aug. 21, 2003 claiming priority of U.S. Provisional Application No. 60/405,222 filed Aug. 22, 2002.

FIELD OF THE INVENTION

The present invention relates to the synthesis of 2-chloro-1,1,1,2,3,3,3-heptafluoropropane and its integration into the manufacture of hexafluoriopropene and 1,1,1,2,3,3,3-heptafluoropropane.

BACKGROUND

The compound 2-chloro-1,1,1,2,3,3,3-heptafluoropropane ($CF_3CClFCF_3$, CFC-217ba) is a useful intermediate for the preparation of hexafluoropropene ($C_3F_6$, HFP), a valuable fluoromonomer, and 1,1,1,2,3,3,3-heptafluoropropane ($CF_3CHFCF_3$, HFC-227ea), a fire extinguishant and propellant.

Commercial methods for the preparation of hexafluoropropene typically involve operating temperatures of greater than about 600° C. The high reaction temperatures lead to the formation of perfluoroisobutylene, an extremely toxic compound that is costly to remove and destroy (e.g., see European Patent Publication No. 002 098 B1). Processes for the manufacture of HFP at lower temperatures based on the use of acyclic three-carbon hydrocarbons or partially halogenated three-carbon hydrocarbons are disclosed in U.S. Pat. Nos. 5,043,491, 5,057,634 and 5,068,472.

U.S. Pat. No. 6,018,083 discloses a process for manufacture of HFP and HFC-227ea comprising (a) feeding $CCl_2=CClCF_3$, HF and $Cl_2$ to a first reaction zone containing a catalyst comprising trivalent chromium and operating at a temperature of at least 250° C. but not more than 325° C. to produce a reactor effluent comprising $C_3Cl_3F_5$, $C_3Cl_2F_6$ and CFC-217ba, HCl and HF; (b) distilling the reactor effluent of (a) to produce (i) a low boiling stream comprising HCl, (ii) a reactant stream comprising an azeotrope of CFC-217ba and HF and (iii) a high boiling stream comprising $C_3Cl_3F_5$ and $C_3Cl_2F_6$; (c) reacting the CFC-217ba of reactant stream (ii) with hydrogen in the presence of a catalyst to produce a mixture comprising HFP and HFC-227ea; (d) feeding the $C_3Cl_3F_5$ and $C_3Cl_2F_6$ of high-boiling stream (iii) along with HF to a second reaction zone containing a catalyst comprising trivalent chromium and operating at a temperature of at least about 375° C. to produce a reaction product comprising CFC-217ba and HF; and (e) recycling the reaction product of (d) to the first reaction zone. U.S. Pat. No. 3,865,885 discloses the catalytic chlorofluorination of $CH_3CHFCH_3$ to $CCl_2=CClCF_3$; WO PCT 99/51555 discloses processes for the purification and use of CFC-217ba (e.g., dehalogenation of CFC-217ba to make HFP or hydodechlorination of CFC-217ba to make HFC-227ea) and azeotropes of CFC-217ba with HF; and U.S. Pat. No. 5,364,992 discloses the hydrogenolysis of halocarbons (e.g., CFC-217ba).

There remains a need for methods of manufacturing CFC-217ba.

SUMMARY OF THE INVENTION

This invention provides a process for the preparation of 2-chloro-1,1,1,3,3,3-heptafluoropropane. The process comprises (a) contacting a mixture comprising hydrogen fluoride (HF), chlorine ($Cl_2$), and at least one starting material selected from the group consisting of halopropenes of the formula $CX_3CCl=CX_2$ and halopropanes of the formula the $CX_3CClYCX_3$, wherein each X is independently selected from the group consisting of F and Cl, and Y is selected from the group consisting of H, Cl and F (provided that the number of X and Y which are F totals no more than six) with a chlorofluorination catalyst in a reaction zone to produce a product mixture comprising $CF_3CClFCF_3$, HCl, HF, and underfluorinated halogenated hydrocarbon intermediates. The process is characterized by said chlorofluorination catalyst comprising at least one chromium-containing component selected from (i) a crystalline alpha-chromium oxide where at least 0.05 atom % of the chromium atoms in the alpha-chromium oxide lattice are replaced by nickel, trivalent cobalt or both nickel and trivalent cobalt, provided that no more than 2 atom % of the chromium atoms in the alpha-chromium oxide lattice are replaced by nickel and that the total amount of chromium atoms in the alpha-chromium oxide lattice that are replaced by nickel and trivalent cobalt is no more than 6 atom %, and (ii) a fluorinated crystalline oxide of (i).

This invention also provides a process for the manufacture of a mixture of HFC-227ea and hexafluoropropene by reacting a starting mixture comprising CFC-217ba and hydrogen in the vapor phase at an elevated temperature, optionally in the presence of a hydrogenation catalyst. This process is characterized by preparing the CFC-217ba by the process described above.

DETAILED DESCRIPTION

In the chlorofluorination step of the process of this invention, one or more halopropene compounds having the formula $CX_3CCl=CX_2$ and halopropanes of the formula the $CX_3CClYCX_3$ are typically reacted with chlorine ($Cl_2$) and substantially anhydrous hydrogen fluoride (HF). Suitable halopropene starting materials for the process of this invention include $CCl_3CCl=CCl_2$ (HCP), $CCl_2FCCl=CCl_2$, $CClF_2CCl=CCl_2$, $CF_3CCl=CCl_2$ (CFC-1213xa), E- and Z-$CF_3CCl=CClF$, and $CF_3CCl=CF_2$ (CFC-1215xc). HCP may be prepared by the reaction of tetrachloroethene with chloroform in the presence of aluminum chloride to give 1,1,1,2,2,3,3-heptachloropropane which in turn is treated with base as described by Prins in *Journal fuer Praktische Chemie*, Volume 89, pages 414–424 (1914). CFC-1213xa may be prepared by chlorofluorination of isopropyl fluoride as disclosed in U.S. Pat. No. 3,865,885. CFC-1215xc may be prepared by fluorination of CFC-1213xa in the presence of a chromium (III) oxide catalyst and a divalent zinc compound as disclosed in U.S. Pat. No. 3,878,257. Suitable halopropane starting materials for the process of this invention include $CF_3CCl_2CCl_3$ (CFC-213ab), $CF_3CCl_2CCl_2F$ (CFC-214ab), $CF_3CHClCClF_2$ (HCFC-225da) and $CF_3CHClCF_3$ (HCFC-226da). CFC-213ab and CFC-214ab may be prepared by chlorofluorination of propane or propylene as disclosed in U.S. Pat. No. 5,057,634. HCFC-225da and HCFC-226da may be prepared by reaction of CFC-1213xa with HF and antimony pentachloride as described by McBee et al. in *Journal of American Chemical Society*, Vol. 70, pages 2023–2024 (1948).

Preferably, the reaction of HF and $Cl_2$ with the halopropene(s) $CX_3CCl=CX_2$ and/or the halopropane(s) $CX_3CClYCX_3$, is carried out in the vapor phase in a heated tubular reactor. A number of reactor configurations are possible including horizontal or vertical orientation of the reactor and different modes of contacting the halopropene starting materials with HF and chlorine.

In one embodiment of the invention, the starting halopropene(s) $CX_3CCl=CX_2$ and/or the halopropane(s) $CX_3CClYCX_3$ may be initially vaporized and fed to the reactor as gas.

In another embodiment of the invention, the starting halopropene(s) $CX_3CCl=CX_2$ and/or the halopropane(s) $CX_3CClYCX_3$ may be contacted with HF in a pre-reactor. The pre-reactor may be empty, but is preferably filled with a suitable packing such as Monel™ or Hastelloy™ nickel alloy turnings or wool, or other material inert to HCl and HF which allows for efficient mixing of the $CX_3CCl=CX_2$ and/or $CX_3CClYCX_3$ and the HF vapor.

Suitable temperatures for the pre-reactor are within the range of from about 80° C. to about 250° C., preferably from about 100° C. to about 200° C. For starting materials having fewer than three fluorine substituents, some substitution of chlorine substituents by fluorine may occur in the pre-reactor. Higher temperatures result in greater conversion of the halopropene(s) $CX_3CCl=CX_2$ and/or the halopropane(s) $CX_3CClYCX_3$ in the pre-reactor and a greater degree of fluorination in the converted products. Under these conditions, for example, hexachloropropene is converted to a mixture containing predominantly CFC-1213xa.

The term "degree of fluorination" reflects the number of fluorine substituents that replace chlorine substituents in the $CX_3CClYCX_3$ and $CX_3CCl=CX_2$ starting materials. For example, $CF_3CCl=CClF$ represents a higher degree of fluorination than $CClF_2CCl=CCl_2$ and $CF_3CCl_2CF_3$ represents a higher degree of fluorination than $CCl_2FCCl_2CF_3$. The term "underfluorinated halogenated hydrocarbon intermediates" means halopropanes of the formula $CX_3CClYCX_3$ and halopropenes of the formula $CX_3CCl=CX_2$ wherein the number of X and Y which are F totals no more than six. Examples of underfluorinated intermediates are $CCl_2=CClCCl_3$, $CClF=CClCF_3$, $CCl_2=CClCClF_2$, $CCl_2=CClCF_3$, $CF_2=CClCF_3$, $CCl_2=CClCCl_2F$, $CF_3CCl_2CCl_3$, $CF_3CCl_2CCl_2F$, $CF_3CHClCClF_2$, and $CF_3CHClCF_3$ (i.e., the same compounds suitable as starting materials). Underfluorinated halogenated hydrocarbon intermediates may include unreacted starting material, but do not include either CFC-217ba (i.e., the desired product) or 1-chloroheptafluoropropane (i.e., CFC-217ca).

The molar ratio of HF to the $CX_3CCl=CX_2$ and/or $CX_3CClYCX_3$ starting material in the pre-reactor is typically from about the stoichiometric ratio of HF to halopropene to about 50:1. The stoichiometric ratio of HF to the starting material depends on whether the starting material is a halopropene or a halopropane, or a mixture, and the average degree of fluorination of the starting material fed to the pre-reactor. For example, if the halopropene is HCP and the desired final product is CFC-217ba, the stoichiometric ratio of HF to HCP is 7:1; if the halopropene is CFC-1213xa, the stoichiometric ratio of HF to CFC-1213xa is 4:1; and if the halopropane is CFC-214ab, the stoichiometric ratio of HF to CFC-214ab is 3:1. Preferably, the molar ratio of HF to starting material in the pre-reactor is from about twice the stoichiometric ratio of HF to halopropane or halopropene to about 40:1. Higher molar ratios of HF to starting material are not particularly beneficial. Lower ratios result in reduced yields of CFC-217ba unless additional HF is co-fed to the reaction zone.

If the starting materials are contacted with HF in a pre-reactor, the effluent from the pre-reactor is contacted with chlorine in the reaction zone of step (a).

In another embodiment of the invention, the starting material(s) may be contacted with $Cl_2$ in a pre-reactor, optionally in the presence of HF. The pre-reactor may be empty, but is preferably filled with a suitable packing such as Monel™ or Hastelloy™ nickel alloy turnings or wool, activated carbon, or other material inert to HCl and $Cl_2$ which allows for efficient mixing of the $CX_3CClYCX_3$ and/or $CX_3CCl=CX_2$ and the $Cl_2$ vapor.

Typically at least a portion of any halopropene starting material reacts with $Cl_2$ in the pre-reactor by addition to the olefinic bond to give a saturated halopropane. In addition, if HF is present, it may also react in the pre-reactor. Suitable temperatures for the pre-reactor in this embodiment of the invention are within the range of from about 80° C. to about 250° C., preferably from about 100° C. to about 200° C. Higher temperatures result in greater conversion of the halopropene starting material to saturated products and a greater degree of halogenation. In the presence of HF, the degree of fluorination will also increase at higher pre-reactor temperatures.

The term "degree of halogenation" reflects the total number of halogen substituents (chlorine plus fluorine) in a halopropane or halopropene product. For example, $CF_3CCl_2CClF_2$ has a higher degree of halogenation than $CF_3CCl=CCl_2$. Also, $CF_3CClFCF_3$ has a higher degree of halogenation than $CF_3CHClCF_3$.

The molar ratio of $Cl_2$ to starting material fed to either the pre-reactor or the reaction zone of step (a) is typically from about 1:1 to about 10:1, preferably from about 1:1 to about 5:1.

In a preferred embodiment of the invention, in the chlorfluorination step the starting materials are vaporized, preferably in the presence of HF, and contacted with HF and $Cl_2$ in a pre-reactor and then fed to a reaction zone. If the preferred amounts of HF and $Cl_2$ are fed in the pre-reactor, additional HF and $Cl_2$ are not required in the reaction zone. Suitable temperatures in the reaction zone are within the range of from about 280° C. to not more than 450° C., preferably from about 300° C. to about 425° C. Higher temperatures result in greater conversion of the starting materials, but also contribute to reduced catalyst life. Lower temperatures than about 280° C. result in yields of CFC-217ba often below 10%, and increased amounts of dichlorohexafluoropropane isomers. Nevertheless, the dichlorohexafluoropropane isomers may be subsequently separated from CFC-217ba and recycled back to the reaction zone.

Suitable reactor pressures for vapor phase embodiments of this invention may be in the range of from about 1 to about 30 atmospheres. Reactor pressures of about 5 atmospheres to about 30 atmospheres may be advantageously employed to facilitate separation of HCl from other reaction products in step (b) of the process.

The reaction zone of the chlorofluorination step of the process of the invention may contain a chlorofluorination catalyst comprising a crystalline metal-substituted alpha-chromium oxide where trivalent cobalt and/or nickel is substituted for chromium in the chromium oxide lattice. The amount of nickel should be no more than 2 atom % based on the lattice positions of the alpha-chromium oxide occupied by chromium (before substitution), and the amount of cobalt should be no more than 6 atom % based on the lattice positions of the alpha-chromium oxide occupied by chromium (before substitution). Also, the amount of cobalt, nickel, or both nickel and cobalt should occupy at least 0.05 atom %, but the total amount of cobalt and nickel together should occupy no more than 6 atom % based on the lattice positions of the alpha-chromium oxide occupied by chromium (before substitution). Accordingly, the metal-substituted chromium oxides may be represented by the general formula α-Ni$_x$Co$_y$Cr$_{2-x-y}$O$_3$ where x is from 0 to 0.04; y is from 0 to 0.12; x, y or each of x and y is at least 0.001; and x+y totals from 0.001 to 0.12. Crystalline oxides of this formula may be fluorinated before use in the reaction zone. Further information on the cobalt-substituted alpha-chromium oxides useful for this invention is provided in U.S. Patent Application 60/405,220 [CL2099 US PRV] filed Aug. 22, 2002, and hereby incorporated by reference herein in its entirety. Further information on the nickel-substituted alpha-chromium oxides and mixed nickel- and cobalt- substituted alpha-chromium oxides useful for this invention is provided in U.S. Patent Application 60/405,221 [CL2100 US PRV] filed Aug. 22, 2002, and hereby incorporated by reference herein in its entirety.

These cobalt/nickel/chromium oxide compositions may be prepared by co-precipitation from aqueous solutions of the respective cobalt(II), cobalt(III), nickel(II), and chromium(III) salts. Preferably, the cobalt, nickel, and chromium salts are co-precipitated by adding ammonium hydroxide (aqueous ammonia) to an aqueous solution of soluble salts. The concentration of divalent or trivalent cobalt and/or the concentration of divalent nickel should be at least about 0.05 mole % of the total of cobalt, nickel, and chromium in the solution, provided that the concentration of divalent nickel should be no more than from about 2 mole % of the total of cobalt, nickel, and chromium in the solution and the total concentration of divalent or trivalent cobalt and divalent nickel should be no more than about 6 mole %. The solution should contain at least three moles of nitrate (i.e., NO$_3^-$) per total mole of chromium (i.e., Cr$^{3+}$). At least three moles of ammonium (i.e., NH$_4^+$) per mole of chromium (i.e., Cr$^{3+}$) should be added before the co-precipitated solid is collected. After precipitation is complete, water is evaporated from the mixture, and the resulting solid is dried and calcined as discussed in the two concurrently filed patent applications referenced above and incorporated herein by reference.

Of note are preparations where excess ammonium nitrate (i.e., more than three moles of ammonium nitrate per mole of chromium) is present in the aqueous solution. For example, in addition to the ammonium nitrate already present from reaction of ammonium hydroxide with chromium nitrate, from about 0.1 mole to about 7.0 moles of additional ammonium nitrate per mole of chromium may be added to the solution before, during, or after the co-precipitation of the compositions. The addition of excess ammonium nitrate to the precipitated mixture of cobalt, nickel, and chromium hydroxides prior to the dehydration step may be used to decrease the particle size of the formula α-Ni$_x$Co$_y$Cr$_{2-x-y}$O$_3$ phase which in turn increases the surface area of that phase and the activity of the catalyst (see PREPARATION EXAMPLES 9 and 11 and EXAMPLES 9 and 10).

After the ammonium nitrate is added to the mixture, it is preferably stirred for about 0.5 to ten hours (more preferably one to five hours) at a temperature of from about 20° C. to about 60° C. The mixture is then dried and calcined.

Other agents that serve this purpose include aqueous hydrogen peroxide (1% to 30% solutions), ozone, peroxy acids such as peroxyacetic acid, and ammonium persulfate. Agents such as halogens may be used, but are not preferred. Agents containing alkali metals such as potassium persulfate or sodium perborate may also be used but are not preferred.

After the precipitation of the mixture of cobalt, nickel, and chromium hydroxides is complete, and excess ammonium nitrate or other agents added if desired, the mixture is dried by evaporation.

Optionally, the precipitated mixture of cobalt, nickel, and chromium hydroxides may be collected and, if desired, washed with deionized water before drying. This may influence the activity of the catalyst (see PREPARATION EXAMPLES 7 and 8 and EXAMPLES 7 and 8).

After the cobalt, nickel, and chromium hydroxide mixture has been dried, the nitrate salts are then decomposed by heating the solid from about 250° C. to about 350° C. The resulting solid is then calcined at temperature of from about 375° C. to about 1000° C., preferably from about 400° C. to about 600° C. Lower calcination temperatures may result in the presence of some residual nitrate impurities in the metal oxide. The calcination temperature can influence the activity of the catalysts and, in turn, the product distribution when the catalysts are used to change the fluorine distribution in hydrocarbons and halogenated hydrocarbons (see PREPARATION EXAMPLES 3, 4, 9, AND 10 and EXAMPLES 3, 4, 9, and 11).

The calcination is preferably carried out in the presence of oxygen, most preferably in the presence of air.

After calcination, the resulting metal-substituted crystallites are typically not visually distinguishable from formula α-Cr$_2$O$_3$ by transmission electron microscopy. Furthermore, X-ray and electron diffraction studies are typically entirely consistent with the formula α-Cr$_2$O$_3$ structure with some lattice contraction proportional to the amount of Co(III) substituted for Cr(III) in the structure, and with some lattice expansion or contraction proportional to the amount of and Ni(II) and Ni(III), respectively, substituted for Cr(III) in the structure. Further details on the characterization of these compositions are provided in the two concurrently filed patent applications referenced above and incorporated herein by reference. The metal content of the chromium oxide compositions of the present invention effects the activity of the catalyst obtained after fluorinating the mixed metal oxide. For example, in the chlorofluorination of CCl$_2$=CClCF$_3$ to CF$_3$CClFCF$_3$, the activity of the fluorinated metal oxide catalysts for formation of CF$_3$CClFCF$_3$ at temperatures of about 400° C. is improved for those compositions having nominally 1–3 atom % cobalt and/or up to 2 atom % nickel in the catalyst relative to a chromium oxide catalyst having no added metals (see TABLE 1).

TABLE 1

Activity of Fluorinated Metal-Substituted Chromium Oxides for Chlorofluorination of CCl$_2$=CClCF$_3$ to CF$_3$CClFCF$_3$[a]

| Nominal Cr/Co/Ni Ratio | Catalyst Calcination Temperature | Reactor Temperature | % CF$_3$CClFCF$_3$ in Product |
| --- | --- | --- | --- |
| 100/0/0 | 400° C. | 400° C. | 24.1 |
| 99/1/0 | 400° C. | 400° C., washed | 47.4 |
| 98/2/0 | 400° C. | 400° C. | 46.6 |
| 98/2/0 | 550° C. | 400° C. | 36.7 |
| 98/2/0 | 900° C. | 400° C. | 14.8[b] |
| 98/0/2 | 400° C. | 375° C. | 27.4 |
| 97/3/0 | 400° C. | 400° C., washed | 31.7 |
| 95/3/2 | 400° C. | 375° C., excess NH$_4$NO$_3$ | 34.0 |

[a]Catalysts were prepared by co-precipitation technique using ammonia. Molar feed ratios of HF, 1213xa, and Cl$_2$ = 30:1:2. The contact time is 15 seconds.
[b]Molar feed ratios of HF, 1213xa, and Cl$_2$ = 20:1:4.

Nickel chromium spinel (nickel chromite, NiCr$_2$O$_4$) served as a catalyst for conversion of CFC-1213xa to CFC-215aa (CF$_3$CCl$_2$CClF$_2$) with good selectivity while cobalt chromium spinel (cobalt chromite, CoCr$_2$O$_4$) did not (see COMPARATIVE EXAMPLES 16 and 17).

The catalytic compositions employed in this invention may further comprise one or more additives in the form of metal compounds that alter the selectivity or activity of the crystalline metal-substituted alpha-chromium oxides or the fluorinated metal oxide catalysts containing chromium, cobalt, and/or nickel. Suitable additives may be selected from the group consisting of fluorides, oxides, or oxyfluoride compounds of Mg, Ca, Sc, Y, La, Ti, Zr, Hf, V, Nb, Ta, Mo, W, Mn, Re, Fe, Ru, Co, Rh, Ir, Ni, Pd, Pt, Cu, Ag, Au, Ce, and Zn.

The total content of the additive(s) in the compositions of the present invention may be from about 0.05 atom % to about 15 atom % based on the total metal content of the compositions. The additives may be incorporated into the compositions of the present invention by standard procedures such as the impregnation technique.

Generally, the calcined compositions will be pre-treated with a fluorinating agent prior to use as catalysts for changing the fluorine content of halogenated carbon compounds. Typically this fluorinating agent is HF though other materials may be used such as sulfur tetrafluoride, carbonyl fluoride, and fluorinated carbon compounds such as trichlorofluoromethane, dichlorodifluoromethane, chlorodifluoromethane, trifluoromethane, or 1,1,2-trichlorotrifluoroethane. This pretreatment can be accomplished, for example, by placing the catalyst in a suitable container which can be the reactor to be used to perform the process in the instant invention, and thereafter, passing HF over the dried, calcined catalyst so as to partially saturate the catalyst with HF. This is conveniently carried out by passing HF over the catalyst for a period of is time, for example, about 0.1 to about 10 hours at a temperature of, for example, about 200° C. to about 450° C.

Examples of compounds produced in step (a) of the process of this invention include $CF_3CClFCF_3$ (CFC-217ba) and HCl in addition to underfluorinated halogenated propanes and propenes including $CF_3CHClCF_3$ (HCFC-226da), $CF_3CCl_2CF_3$ (CFC-216aa), $CF_3CClFCClF_2$ (CFC-216ba), $CF_3CCl_2CClF_2$ (CFC-215aa), $CF_3CClFCCl_2F$ (CFC-215bb), $CF_3CCl_2CCl_2F$ (CFC-214ab), and $CF_3CCl=CF_2$ (CFC-1215xc).

This process allows unreacted starting material and other underfluorinated intermediates to be recycled to the reactor for the production of additional CFC-217ba. For example the chlorofluorination step (step(a)) may be advantageously followed by a separation step (step (b)) separating the product of step (a) to recover $CF_3CClFCF_3$ as a product and to obtain underfluorinated halogenated hydrocarbon intermediates; and a recycle step (step (c)) returning underfluorinated halogenated hydrocarbon intermediates obtained in step (b) back to the step (a) reaction zone.

In step (b) of the process of the invention, the effluent from the reaction zone in step (a) comprising $CF_3CClFCF_3$ (CFC-217ba), HCl, HF, and the underfluorinated halogenated propanes and propenes, is delivered to one or more separation zones in which $CF_3CClFCF_3$ with its azeotropic HF, is separated from the HCl, excess HF, and underfluorinated halogenated propanes and propenes. The separation zones may comprise conventional chemical processing equipment such as, but not limited to, scrubbers, decanters, and/or distillation columns. The CFC-217ba is recovered. The CFC-217ba/HF azeotrope as well as recovery of HF and CFC-217ba from said azeotrope is disclosed in International Patent Application WO 99/51555 the teachings of which are hereby incorporated by reference.

In step (c) of the process of this invention, underfluorinated halogenated propanes and propenes, as well as excess HF obtained in the separation zone(s) may be returned to step (a). Limited amounts of CFC-217ba and CFC-217ca may also be returned to the reaction zone.

The reaction zone and its associated feed lines, effluent lines, and associated units should be constructed of materials resistant to hydrogen fluoride and hydrogen chloride. Typical materials of construction, well-known to the fluorination art, include stainless steels, in particular of the austenitic type, the well-known high nickel alloys, such as Monel™ nickel-copper alloys, Hastelloy™ nickel-based alloys and, Inconel™ nickel-chromium alloys, and copper-clad steel.

The product of this invention, 2-chloro-1,1,1,2,3,3,3-heptafluoropropane (CFC-217ba), is useful as an intermediate for commercially valuable fluorocarbons. For example, hydrodechlorination of CFC-217ba gives either hexafluoropropene, a useful polymer intermediate, or 1,1,1,2,3,3,3-heptafluoropropane (HFC-227ea), which finds application as a propellant and fire extinguishant. Fluorination of CFC-217ba gives octafluoropropane (FC-218) which is useful as an etchant in the electronics industry.

The use of CFC-217ba as a starting material for reaction with $H_2$ is well known. For example, CFC-217ba can be converted to a product comprising HFC-227ea and HFP by contacting the CFC-217ba with hydrogen at an elevated temperature in the vapor phase over a catalyst comprising at least one metal selected from the group consisting of rhenium, ruthenium, rhodium and palladium. The reaction temperature for these metal containing catalysts is at least about 100° C. Further details and other methods of hydrodechlorination of CFC-217ba are described in U.S. Pat. No. 6,018,083. CFC-217ba can also be converted to a product comprising HFC-227ea and HFP by contacting the CFC-217ba with hydrogen at an elevated temperature in an empty reaction vessel of nickel, iron or their alloys at a pressure of from 0 to 69 atmospheres and a temperature of from 350° C. to 700° C. as disclosed on U.S. Pat. No. 5,364,992.

Without further elaboration, it is believed that one skilled in the art can, using the description herein, utilize the present invention to its fullest extent. The following specific embodiments are, therefore, to be construed as merely illustrative, and do not constrain the remainder of the disclosure in any way whatsoever.

EXAMPLES

Catalyst Preparation

Comparative Preparation Example 1

Preparation of 100% Chromium Catalyst (400° C.)

A solution of 400 g $Cr(NO_3)_3[9(H_2O)]$ (1.0 mole) in 1000 mL of deionized water was treated dropwise with 477 mL of 7.4M aqueous ammonia raising the pH to about 8.5. The slurry was stirred at room temperature overnight. After re-adjusting the pH to 8.5 with ammonia, the mixture was poured into evaporating dishes and dried in air at 120° C. The resulting solid was then calcined in air at 400° C. for 24 hours.

Preparation Example 2

Preparation of 99% Chromium/1% Cobalt Catalyst (Washed; 400° C.)

A solution of 792.29 g $Cr(NO_3)_3[9(H_2O)]$ (1.98 moles) and 5.82 g $Co(NO_3)_2[6(H_2O)]$ (0.0200 mole) was prepared in 2000 mL of deionized water. The solution was treated dropwise with 955 mL of 7.4M aqueous ammonia which raised the pH to about 8.5. The slurry was stirred at room temperature overnight. The pH was adjusted to 8.5 the following day. The solid was then collected using two fritted funnels; the resulting solid in each funnel was washed with 15–20 liters of deionized water. The solids were dried in air at 120° C. for 24 hours and then calcined in air at 400° C. for 24 hours.

Preparation Example 3

Preparation of 98% Chromium/2% Cobalt Catalyst
(400° C.)

A solution of 784.30 g $Cr(NO_3)_3[9(H_2O)]$ (1.96 moles) and 11.64 g $Co(NO_3)_2[6(H_2O)]$ (0.040 mole) was prepared in 2000 mL of deionized water. The solution was treated dropwise with 950 mL of 7.4M aqueous ammonia which raised the pH from about 1.8 to about 8.5. The slurry was stirred at room temperature overnight and then evaporated to dryness in air at 110–120° C. for 48 hours. The dried catalyst was divided in half. One half was calcined in air at 400° C. for 24 hours.

Preparation Example 4

Preparation of 98% Chromium/2% Cobalt Catalyst
(900° C.)

The other half of the dried catalyst prepared in PREPARATION EXAMPLE 3 was calcined in air at 900° C. for 24 hours.

Preparation Example 5

Preparation of 98% Chromium/2% Cobalt Catalyst
(550° C.)

A solution of 1,010 g $Cr(NO_3)_3[9(H_2O)]$ (2.52 moles) and 14.6 g $Co(NO_3)_2[6(H_2O)]$ (0.050 mole) was prepared in 1000 mL of deionized water. The green solution was evaporated at a temperature of about 100° C. until a thick, black precipitate formed. The solid was dried at 300–325° C. on a hot plate. The solid was then transferred to a porcelain dish and calcined in a furnace at 550° C. for 20 hours.

Preparation Example 6

Preparation of 98% Chromium/2% Cobalt Catalyst
(550° C.)

A solution of 1,010 g $Cr(NO_3)_3[9(H_2O)]$ (2.52 moles) and 14.6 g $Co(NO_3)_2[6(H_2O)]$ (0.0502 mole) was prepared in 1500 mL of deionized water. The solution was treated with 500 mL of 29 weight percent aqueous ammonia with mixing provided by a mechanical stirrer. The mixture was stirred for two hours and the pH stabilized at 6.0. The mixture was transferred to a large, ceramic dish. Water was driven off by heating. After most of the water had evaporated, the sample was heated to 250–300° C. on a hot plate. The resulting solid was then transferred to a porcelain dish and calcined in a furnace at 550° C. for 20 hours.

Preparation Example 7

Preparation of 97% Chromium/3% Cobalt Catalyst
(Unwashed; 400° C.)

A solution of 776.29 g $Cr(NO_3)_3[9(H_2O)]$ (1.94 moles) and 17.46 g $Co(NO_3)_2[6(H_2O)]$ (0.060 mole) was prepared in 2000 mL of deionized water. The solution was treated dropwise with 950 mL of 7.4M aqueous ammonia until the pH reached about 8.5. The slurry was stirred at room temperature for 24 hours and then evaporated to dryness in air at 110–120° C. The dried catalyst was ground to a powder and then calcined in air at 400° C. for 24 hours.

Preparation Example 8

Preparation of 97% Chromium/3% Cobalt Catalyst
(Washed; 400° C.)

A solution of 776.29 g $Cr(NO_3)_3[9(H_2O)]$ (1.94 moles) and 17.46 g $Co(NO_3)_2[6(H_2O)]$ (0.060 mole) was prepared in 2000 mL of deionized water. The solution was treated dropwise with 955 mL of 7.4M aqueous ammonia which raised the pH to about 8.5. The slurry was stirred at room temperature overnight and the pH adjusted to 8.5 the following day. The solid was collected in two 3 L fritted funnels and each portion washed with 15–20 L of deionized water. The washed solid was then evaporated to dryness in air at 120° C. for 24 hours and then calcined in air at 400° C. for 24 hours.

Preparation Example 9

Preparation of 95% Chromium/5% Cobalt Catalyst
(400° C.)

A solution of 760.28 g $Cr(NO_3)_3[9(H_2O)]$ (1.90 moles) and 29.10 g $Co(NO_3)_2[6(H_2O)]$ (0.10 mole) was prepared in 2000 mL of deionized water. The solution was treated dropwise with 950 mL of 7.4M aqueous ammonia which raised the pH to about 8.5. The slurry was stirred at room temperature overnight and then evaporated to dryness in air at 110–120° C. for 48 hours. The dried catalyst was divided in half. One half was calcined in air at 400° C. for 24 hours.

Preparation Example 10

Preparation of 95% Chromium/5% Cobalt Catalyst
(900° C.)

The other half of the dried catalyst prepared in PREPARATION EXAMPLE 9 was calcined in air at 900° C. for 24 hours.

Preparation Example 11

Preparation of 95% Chromium/5% Cobalt Catalyst (1.6 Eq. of Excess $NH_4NO_3$; 400° C.)

A solution of 760.28 g $Cr(NO_3)_3[9(H_2O)]$ (1.90 moles) and 29.10 g $Co(NO_3)_2[6(H_2O)]$ (0.10 mole) was prepared in 2000 mL of deionized water. The solution was treated dropwise with 950 mL of 7.4M aqueous ammonia; the pH reached 8.5. The slurry was stirred at room temperature for 24 hours and then treated with a solution of 240.12 g $NH_4NO_3$ (3.0 moles). After stirring at room temperature for 2 hours, the mixture was evaporated to dryness in air at 120° C. and held at that temperature over the weekend. The dried catalyst was ground to a powder with a mortar and pestle and then calcined in air at 400° C. for 24 hours.

Preparation Example 12

Preparation of 90% Chromium/10% Cobalt Catalyst
(Washed; 400° C.)

A solution of 720.27 g $Cr(NO_3)_3[9(H_2O)]$ (1.80 moles) and 58.21 g $Co(NO_3)_2[6(H_2O)]$ (0.20 mole) was prepared in 2000 mL of deionized water. The solution was treated dropwise with 955 mL of 7.4M aqueous ammonia which raised the pH from about 2.1 to about 8.5. The slurry was stirred at room temperature overnight. The following day, the pH was the increased from 8.05 to 8.5 by addition of aqueous ammonia. The solid was collected in two 3 L fritted funnels and each portion washed with 15–20 L of deionized water. The washed solid was then evaporated to dryness in air at 120° C. for 24 hours. The dried catalyst was then calcined in air at 400° C. for 24 hours.

Preparation Example 13

Preparation of 90% Chromium/10% Cobalt Catalyst (3.3 Eq. of Excess $NH_4NO_3$; 400° C.)

A solution of 72.03 g $Cr(NO_3)_3[9(H_2O)]$ (0.18 mole) and 5.82 g $Co(NO_3)_2[6(H_2O)]$ (0.020 mole) was prepared in 200 mL of deionized water. The solution was brought to pH 8.5 treatment with 7.4M aqueous ammonia. The slurry was stirred at room temperature for 24 hours. The mixture was then treated with a solution of 48.02 g of $NH_4NO_3$ (0.60 mole) dissolved in 100 mL of water. The slurry was stirred for one hour and then dried at 120° C. in air for about 90 hours. The dried solid was crushed to a powder and then placed in covered dish and calcined at 400° C. for 24 hours in air.

Preparation Example 14

Preparation of 90% Chromium/10% Cobalt Catalyst (6.7 Eq. of Excess $NH_4NO_3$; 400° C.)

PREPARATION EXAMPLE 13 was repeated except that the mixture of chromium/cobalt oxide/hydroxides was treated with a solution of 96.05 g of $NH_4(NO_3)$ (1.2 moles) dissolved in 200 mL of water.

Preparation Example 15

Preparation of 98% Chromium/2% Nickel Catalyst
(400° C.)

A solution of 588.3 g $Cr(NO_3)_3[9(H_2O)]$ (1.47 moles) and 8.72 g (0.030 mole) $Ni(NO_3)_2[6(H_2O)]$ dissolved in 1.5 L of deionized water was treated with 7.4M aqueous ammonia until the pH reached 8.5. The addition of ammonia took 1.5 hours. The slurry was stirred at room temperature for 24 hours; ammonia was added occasionally to keep the pH at about 8.5. The mixture was then evaporated to dryness in air at 110° C. over the course of 40 hours. The dried catalyst was ground to a powder and then calcined in air at 400° C. for 24 hours.

Preparation Example 16

Preparation of 95% Chromium/5% Nickel Catalyst
(400° C.)

The procedure of PREPARATION EXAMPLE 8 was repeated using a solution of 760.3 g $Cr(NO_3)_3[9(H_2O)]$ (1.90 moles) and 29.08 g(0.10 mole) $Ni(NO_3)_2[6(H_2O)]$ dissolved in 2 L of deionized water. After the addition of ammonia and evaporation at 110° C., the solid was calcined in air at 400° C. for 24 hours.

Preparation Example 17

Preparation of 95% Chromium/3% Cobalt/2% Nickel Catalyst (6.2 Eq. of Excess $NH_4NO_3$; 400° C.)

A solution of 380.14 g $Cr(NO_3)_3[9(H_2O)]$ (0.95 mole), 8.73 g $Co(NO_3)_2[6(H_2O)]$ (0.030 mole), and 5.82 g $Ni(NO_3)_2[6(H_2O)]$ (0.020 mole) was prepared in 1000 mL of deionized water. The solution pH was increased from 3.1 to 8.5 by treatment with 7.4M aqueous ammonia. The slurry was stirred at room temperature for 21 hours at pH 8.5. The mixture was then treated with a solution of 472.24 g of $NH_4(NO_3)$ (5.90 moles) dissolved in 500 mL of water. The slurry was stirred for one hour at room temperature and then dried at 110–120° C. in air for about 96 hours. The dried solid was crushed to a powder and then placed in covered crucible and calcined at 400° C. for 24 hours in air.

General Procedure for Chlorofluorination Reactions

The following general procedure was followed in the chlorofluorination of CFC-1213xa using the catalysts prepared as described above.

A weighed quantity of a calcined chromium oxide composition was placed in a was placed in a ⅝" (1.58 cm) diameter Inconel™ nickel alloy reactor tube heated in a fluidized sand bath. The tube was then heated from about 170° C. to about 200° C. in a flow of nitrogen (50 cc/min, $8.3 \times 10^{-7}$ m³/s) over 0.5 hour to 2 hours. HF and nitrogen were then co-fed to the reactor at flow rates of 50 cc/min ($8.3 \times 10^{-7}$ m³/s) each at 175° C. After 0.5 to 2 hours, the HF and nitrogen flow rates were adjusted to 80 cc/min ($1.3 \times 10^{-6}$ m³/s) and 20 cc/min ($3.3 \times 10^{-7}$ m³/s), respectively, and the temperature of the reactor increased to 400–410° C. over a period of 3 to 5 hours. The HF flow was then stopped and the reactor purged with nitrogen at about 300° C. CFC-1213xa was fed from a pump to a vaporizer maintained at about 118° C. The 1213xa vapor was combined with the appropriate molar ratios of HF and chlorine in a ½" (1.27 cm) diameter Monel™ nickel alloy tube packed with Monel™ turnings. The mixture of reactants then entered the reactor; the contact time in the reactor was typically 15 seconds. All reactions were conducted at a nominal pressure of one atmosphere.

General Procedure for Fluorocarbon Product Analysis

The following general procedure is illustrative of the method used for analyzing the products of fluorocarbon reactions. Part of the total reactor effluent was sampled on-line for organic product analysis using a gas chromatograph equipped with a mass selective detector (GC-MS). The gas chromatography was accomplished with a 20 ft. (6.1 m) long×⅛ in. (0.32 cm) diameter tubing containing Krytox® perfluorinated polyether on an inert carbon support. The helium flow was 30 mL/min ($5.0 \times 10^{-7}$ m³/s). Gas chromatographic conditions were 60° C. for an initial hold period of three minutes followed by temperature programming to 200° C. at a rate of 6° C./minute.

The bulk of the reactor effluent containing organic products and also inorganic acids such as HCl and HF was treated with aqueous caustic prior to disposal.

| LEGEND | |
|---|---|
| 13 is CClF$_3$ | 112 is CCl$_2$FCCl$_2$F |
| 113 is CCl$_2$FCClF$_2$ | 114 is CClF$_2$CClF$_2$ |
| 114a is CF$_3$CCl$_2$F | 115 is CF$_3$CClF$_2$ |
| 214ab is CCl$_2$FCl$_2$CF$_3$ | 215aa is CClF$_2$CCl$_2$CF$_3$ |
| 215bb is CCl$_2$FCClFCF$_3$ | 216cb is CF$_3$CF$_2$CClF$_2$ |
| 216aa is CF$_3$CCl$_2$CF$_3$ | 216ba is CClF$_2$CClFCF$_3$ |
| 217ba is CF$_3$CClFCF$_3$ | 217ca is CF$_3$CF$_2$CClF$_2$ |
| 218 is C$_3$F$_8$ | 225da is CF$_3$CHClCClF$_2$ |
| 226da is CF$_3$CHClCF$_3$ | 1213xa is CCl$_2$=CClCF$_3$ |
| 1214 is C$_3$Cl$_2$F$_4$ | 1215xc is CF$_2$=CClCF$_3$ |
| 1225 is C$_3$HF$_5$ | |
| CT is contact time | |

Comparative Example 1

100% Chromium(III) oxide (calcined at 400° C., 27.8 g, 20 mL, −12 to +20 mesh, (1.68 to 0.84 mm)), prepared as described in COMPARATIVE PREPARATION EXAMPLE 1 was placed in a ⅝" (1.58 cm) diameter Inconel™ nickel alloy reactor tube heated in a fluidized sand bath. The chromium oxide was purged with nitrogen and fluorinated following the general procedure. Chlorofluorination of CFC-1213xa began at 300° C. with HF, CFC-1213xa, and chlorine vapor co-fed to the reactor at a contact time of 15 seconds. The GC-MS analyses of the reactor effluent at 300° C., 375° C., and 400° C. with molar feed ratios of 20:1:4 and 30:1:2 are given in Table 2.

Example 2

Cobalt-substituted chromium oxide (Cr/Co 99/1, 29.0 g, 20 mL, −12 to +20 mesh, (1.68 to 0.84 mm)), prepared as described in PREPARATION EXAMPLE 2, was placed in a ⅝" (1.58 cm) diameter Inconel™ nickel alloy reactor tube heated in a fluidized sand bath. The cobalt chromium oxide was purged with nitrogen and fluorinated following the general procedure. Chlorofluorination of CFC-1213xa began at 300° C. with HF, CFC-1213xa, and chlorine co-fed to the reactor at a contact time was 15 seconds. The GC-MS analyses of the reactor effluent at 300° C., 350° C., and 400° C. with molar feed ratios of 20:1:4 and 30:1:2 are given in Table 2.

Example 3

Cobalt-substituted chromium oxide (Cr/Co 98/2, calcined at 400° C., 21.06 g, 15 mL, −12 to +20 mesh, (1.68 to 0.84 mm)), prepared as described in PREPARATION EXAMPLE 3, was placed in a ⅝" (1.58 cm) diameter Inconel™ nickel alloy reactor tube heated in a fluidized sand bath. The cobalt chromium oxide was heated from 77° C. to 176° C. in a flow of nitrogen (50 cc/min, 8.3×10$^{-7}$ m$^3$/s) over the course of about 1.7 hours. HF and N$_2$ were then co-fed to the reactor at a flow rate of 50 cc/min (8.3×10$^{-7}$ m$^3$/s) each. After 1 hour the temperature was then increased to 326° C. over 3 hours while maintaining the HF and N$_2$ flows at 50 cc/min (8.3×10$^{-7}$ m$^3$/s). The N$_2$ and HF flows were then adjusted to 25 cc/min (4.2×10$^{-7}$ m$^3$/s) and 50 cc/min (8.3×10$^{-7}$ m$^3$/s), respectively, while the reactor temperature was increased to 401° C. over 1 hour. The N$_2$ and HF flows were then adjusted to 10 cc/min (1.7×10$^{-7}$ m$^3$/s) and 50 cc/min (8.3×10$^{-7}$ m$^3$/s), respectively, while the reactor temperature was maintained at 401° C. for 1 hour. At the end of this period, the HF flow was stopped and the reactor cooled to 280° C. under 20 sccm (3.3×10$^{-7}$ m$^3$/s) nitrogen flow. Chlorofluorination of CFC-1213xa began at 280° C. with HF, CFC-1213xa, and chlorine vapor co-fed to the reactor at a contact time of 15 seconds. The GC-MS analyses of the reactor effluent at 300° C., 350° C., and 400° C. with molar feed ratios of 20:1:4 and 30:1:2 are given in Table 2.

Example 4

Cobalt-substituted chromium oxide (Cr/Co 98/2, calcined at 900° C., 27.52 g, 15 mL, −12 to +20 mesh, (1.68 to 0.84 mm)), prepared as described in PREPARATION EXAMPLE 4, was placed in a ⅝" (1.58 cm) diameter Inconel™ nickel alloy reactor tube heated in a fluidized sand bath. The cobalt chromium oxide was purged with nitrogen and fluorinated following the general procedure. Chlorofluorination of CFC-1213xa began at 300° C. with HF, CFC-1213xa, and chlorine vapor co-fed to the reactor at a contact time of 15 seconds. The GC-MS analyses of the reactor effluent at 300° C. and 400° C. with a molar feed ratio of 20:1:4 are given in Table 2.

Example 5

Cobalt-substituted chromium oxide (Cr/Co 98/2, calcined at 550° C., 32.0 g, 20 mL, −12 to +20 mesh, (1.68 to 0.84 mm)), prepared as described in PREPARATION EXAMPLE 5, was placed in a ⅝" (1.58 cm) diameter Inconel™ nickel alloy reactor tube heated in a fluidized sand bath. The cobalt chromium oxide was heated from 65° C. to 176° C. in a flow of nitrogen (50 cc/min, 8.3×10$^{-7}$ m$^3$/s) over the course of about 0.8 hour. HF and N$_2$ were then co-fed to the reactor at flow rates of 50 cc/min (8.3×10$^{-7}$ m$^3$/s) each. After 0.6 hour the N$_2$ and HF flows were then adjusted to 20 cc/min (3.3×10$^{-7}$ m$^3$/s) and 80 cc/min (1.3×10$^{-6}$ m$^3$/s), respectively while the reactor temperature was increased to 411° C. over 3 hours. The catalyst was held at 411° C. for 0.75 hour. The N$_2$ and HF flows were then adjusted to 10 cc/min (1.7×10$^{-7}$ m$^3$/s) and 50 cc/min (8.3×10$^{-7}$ m$^3$/s), respectively, while the reactor temperature was maintained at 411° C. for an additional 2 hours. At the end of this period, the HF flow was stopped and the reactor cooled to 295° C. under 15 sccm (2.5×10$^{-7}$ m$^3$/s) nitrogen flow. Hydrogen fluoride, CFC-1213xa, and chlorine were then co-fed to the reactor with a contact time of 15 seconds. The GC-MS analyses of the reactor effluent at 300° C., 350° C., and 400° C. with molar feed ratios of 20:1:4 and 30:1:2 are given in Table 2.

Example 6

Cobalt-substituted chromium oxide (Cr/Co 98/2, calcined at 550° C., 29.4 g, 20 mL, −12 to +20 mesh, (1.68 to 0.84 mm)), prepared as described in PREPARATION EXAMPLE 6, was placed in a ⅝" (1.58 cm) diameter Inconel™ nickel alloy reactor tube heated in a fluidized sand bath. The cobalt chromium oxide was purged with nitrogen and fluorinated following the general procedure. Hydrogen fluoride, CFC-1213xa, and chlorine were then co-fed to the reactor at a contact time of 15 seconds. The GC-MS analyses of the reactor effluent at 300° C., 350° C., and 400° C. with molar feed ratios of 20:1:4 and 30:1:2 are given in Table 2.

Example 7

Cobalt-substituted chromium oxide (Cr/Co 97/3, 31.6 g, 20 mL, −12 to +20 mesh, (1.68 to 0.84 mm)), prepared as described in PREPARATION EXAMPLE 8 was placed in a ⅝" (1.58 cm) diameter Inconel™ nickel alloy reactor tube heated in a fluidized sand bath. The cobalt chromium oxide was purged with nitrogen and fluorinated following the general procedure. Chlorofluorination of CFC-1213xa began at 300° C. with HF, CFC-1213xa, and chlorine vapor co-fed to the reactor at a contact time of 15 seconds. The GC-MS analyses of the reactor effluent at 300° C., 350° C., and 400° C. with molar feed ratios of 20:1:4 and 30:1:2 are given in Table 2.

Example 8

Cobalt-substituted chromium oxide (Cr/Co 97/3, 28.2 g, 20 mL, −12 to +20 mesh, (1.68 to 0.84 mm)), prepared as described in PREPARATION EXAMPLE 7 was placed in a ⅝" (1.58 cm) diameter Inconel™ nickel alloy reactor tube heated in a fluidized sand bath. The cobalt chromium oxide was purged with 25 cc/min ($4.2 \times 10^{-7}$ m$^3$/s) nitrogen at 150 C for 16 hours. The N$_2$ flow was increased to 50 cc/min ($8.3 \times 10^{-7}$ m$^3$/s) at 175 C for 0.5 hour. N$_2$ and HF were then co-fed to the reactor at flow rates of 50 cc/min ($8.3 \times 10^{-7}$ m$^3$/s) each. After 1.2 h, the nitrogen flow was decreased to 20 cc/min ($3.3 \times 10^{-7}$ m$^3$/s) and the HF flow increased to 80 cc/min ($1.3 \times 10^{-6}$ m$^3$/s). The reactor temperature was gradually increased to 300° C. over a 5.7 hours period. The HF was turned off and the reactor purged with 20 cc/min ($3.3 \times 10^{-7}$ m$^3$/s) nitrogen for about 16 hours at 300° C. The flows of N$_2$ and HF were then established at 20 cc/min ($3.3 \times 10^{-7}$ m$^3$/s) and 80 cc/min ($1.3 \times 10^{-6}$ m$^3$/s), respectively, and the reactor temperature increased from 298° C. to 410° C. over 3.5 hours and then held at 410° C. for 2.3 hours. At the end of this period, the HF flow was stopped and the reactor cooled to 300° C. under 20 sccm ($3.3 \times 10^{-7}$ m$^3$/s) nitrogen flow. Chlorofluorination of CFC-1213xa began at 300° C. with HF, CFC-1213xa, and chlorine vapor co-fed to the reactor at a contact time of 15 seconds. The GC-MS analyses of the reactor effluent at 300° C. and 350° C. with molar feed ratios of 20:1:4 and 30:1:2 are given in Table 2.

Example 9

Cobalt-substituted chromium oxide (Cr/Co 95/5, 21.8 g, 15 mL, −12 to +20 mesh, (1.68 to 0.84 mm)), prepared as described in PREPARATION EXAMPLE 9 was placed in a ⅝" (1.58 cm) diameter Inconel™ nickel alloy reactor tube heated in a fluidized sand bath. The cobalt chromium oxide was heated from 52° C. to 173° C. in a flow of nitrogen (50 cc/min, $8.3 \times 10^{-7}$ m$^3$/s) over the course of about 1 hour. HF and nitrogen were then co-fed to the reactor at flow rates of 25 cc/min ($4.2 \times 10^{-7}$ m$^3$/s) and 75 cc/min ($1.25 \times 10^{-6}$ m$^3$/s), respectively. After 2.2 hours, the nitrogen and HF flow rates were adjusted to 50 cc/min ($8.3 \times 10^{-7}$ m$^3$/s) each and the reactor temperature was gradually increased to 299° C. over 3 hours. The reactor was purged with 20 cc/min ($3.3 \times 10^{-7}$ m$^3$/s) nitrogen overnight at 299° C. HF and nitrogen were then co-fed to the reactor at 80 cc/min ($1.3 \times 10^{-6}$ m$^3$/s) and 20 cc/min ($3.3 \times 10^{-7}$ m$^3$/s), respectively for 0.6 hour. The temperature of the reactor was then increased to 400° C. over 2 hours. The nitrogen flow was cut back to 10 cc/min ($1.7 \times 10^{-7}$ m$^3$/s) and the temperature increased to 410° C. After 1 h, the temperature was adjusted to 280° C. Chlorofluorination of CFC-1213xa began at 280° C. with HF, CFC-1213xa, and chlorine vapor co-fed to the reactor at a contact time of 15 seconds. The GC-MS analyses of the reactor effluent at 300° C., 350° C., and 400° C. with a molar feed ratio of 20:1:4 are given in Table 2.

Example 10

Cobalt-substituted chromium oxide pre-treated with excess ammonium nitrate (Cr/Co 95/5, 21.8 g, 15 mL, −12 to +20 mesh, (1.68 to 0.84 mm)), prepared as described in PREPARATION EXAMPLE 11 was placed in a ⅝" (1.58 cm) diameter Inconel™ nickel alloy reactor tube heated in a fluidized sand bath. The cobalt-substituted chromium oxide was purged with nitrogen and fluorinated following the general procedure. Chlorofluorination of CFC-1213xa was begun at 300° C. with HF, CFC-1213xa, and chlorine vapor co-fed to the reactor in a molar ratio of 20:1:4 with a contact time of 15 seconds. The GC-MS analyses of the reactor effluent at 300° C. and 350° C. are given in Table 2.

Example 11

Cobalt-substituted chromium oxide (Cr/Co 95/5, 900° C., 27.3 g, 15 mL, −12 to +20 mesh, (1.68 to 0.84 mm)), prepared as described in PREPARATION EXAMPLE 10 was placed in a ⅝" (1.58 cm) diameter Inconel™ nickel alloy reactor tube heated in a fluidized sand bath. The cobalt chromium oxide was purged with nitrogen and fluorinated following the general procedure. Chlorofluorination of CFC-1213xa began at 300° C. with HF, CFC-1213xa, and chlorine vapor co-fed to the reactor at a contact time of 15 seconds. The GC-MS analyses of the reactor effluent at 350° C. with a molar feed ratio of 20:1:4 is given in Table 2.

Example 12

Cobalt-substituted chromium oxide (Cr/Co 90/10, 900° C., 32.26 g, 20 mL, −12 to +20 mesh, (1.68 to 0.84 mm)), prepared as described in PREPARATION EXAMPLE 12 was placed in a ⅝" (1.58 cm) diameter Inconel™ nickel alloy reactor tube heated in a fluidized sand bath. The cobalt-substituted chromium oxide was heated from 50° C. to 246° C. in a flow of nitrogen (50 cc/min, $8.3 \times 10^{-7}$ m$^3$%s) over the course of about 1.5 hours. The reactor was purged with nitrogen at 20 cc/min ($3.3 \times 10^{-7}$ m$^3$/s) at 174° C. for 16 hours. HF and nitrogen were then co-fed to the reactor at flow rates of 50 cc/min ($8.3 \times 10^{-7}$ m$^3$/s) each at 175° C. for 1.3 hours; during this time there was a noticeable exotherm. HF and nitrogen were then co-fed to the reactor at 80 cc/min ($1.3 \times 10^{-6}$ m$^3$/s) and 20 cc/min ($3.3 \times 10^{-7}$ m$^3$/s), respectively, as the reactor was heated from 175° C. to 403° C. over 4.1 hours. The HF and nitrogen flow rates were then adjusted to 80 cc/min ($1.3 \times 10^{-6}$ m$^3$/s) and 10 cc/min ($1.7 \times 10^{-7}$ m$^3$/s), respectively, as the reactor was heated at 403° C. to 409° C. for an additional 2.3 hours. The HF flow was then ceased and the reactor purged with nitrogen at 300° C. Chlorofluorination of CFC-1213xa began at 300° C. with HF, CFC-1213xa, and chlorine vapor co-fed to the reactor at a contact time of 15 seconds. The GC-MS analyses of the reactor effluent at 300° C. and 350° C. with a molar feed ratio of 20:1:4 are given in Table 2.

Example 13

Nickel-substituted chromium oxide (Cr/Ni 98/2 calcined at 400° C., 29.6 g, 20 mL, −12 to +20 mesh, (1.68 to 0.84 mm)), prepared as described in PREPARATION EXAMPLE 15, was placed in a ⅝" (1.58 cm) diameter Inconel™ nickel alloy reactor tube heated in a fluidized sand bath. The nickel chromium oxide was purged with nitrogen and fluorinated following the general procedure. Chlorofluorination of CFC-1213xa began at 300° C. with HF, CFC-1213xa, Cl₂ vapor co-fed to the reactor in a molar ratio of 20:1:4 with a contact time of 15 seconds. GC-MS analyses of the reactor effluent at 300° C., 350° C., and 375° C. are given in Table 2.

Example 14

Nickel-substituted chromium oxide (Cr/Ni 95/5 calcined at 400° C., 29.2 g, 20 mL, −12 to +20 mesh, (1.68 to 0.84 mm)), prepared as described in PREPARATION EXAMPLE 16, was placed in a ⅝" (1.58 cm) diameter Inconel™ nickel alloy reactor tube heated in a fluidized sand bath. The nickel chromium oxide was purged with nitrogen and fluorinated following the general procedure. Chlorofluorination of CFC-1213xa began at 300° C. with HF, CFC-1213xa, Cl₂ vapor co-fed to the reactor at a contact time of 15 seconds. The GC-MS analyses of the reactor effluent at 300° C., 350° C., and 400° C. with molar feed ratios of 20:1:4 and 30:1:2 are given in Table 2.

Example 15

Cobalt- and nickel-substituted chromium oxide (Cr/Co/Ni 95/3/2, 26.37 g, 19 mL, −12 to +20 mesh, (1.68 to 0.84 mm)), prepared as described in PREPARATION EXAMPLE 17, was placed in a ⅝" (1.58 cm) diameter Inconel™ nickel alloy reactor tube heated in a fluidized sand bath. The nickel cobalt chromium oxide was purged with nitrogen and fluorinated following the general procedure. Chlorofluorination of CFC-1213xa began at 300° C. with HF, CFC-1213xa, Cl₂ vapor co-fed to the reactor at a contact time of 15 seconds. The GC-MS analyses of the reactor effluent at 300° C., 350° C., and 375° C. with molar feed ratios of 20:1:4 and 30:1:2 are given in Table 2.

Comparative Example 16

A commercial sample of cobalt chromite ($CoCr_2O_4$, CAS Reg. No. [12016-69-2], 40.8 g, 20 mL, −12 to +20 mesh, (1.68 to 0.84 mm)),) was pelletized, sieved, and placed in a ⅝" (1.58 cm) diameter Inconel™ nickel alloy reactor tube heated in a fluidized sand bath. The cobalt chromite was purged with nitrogen and fluorinated following the general procedure. Reaction of HF with CFC-1213xa in a molar ratio of 20:1 at 300° C. resulted in less than 2% conversion of the 1213xa to a mixture of CFC-1215xc, -1214, and -215aa. Hydrogen fluoride, CFC-1213xa, and chlorine vapor were then co-fed to the reactor with a contact time of 15 seconds. The GC-MS analysis of the reactor effluent at 375° C. with a molar feed ratio of 30:1:2 is given in Table 2.

Comparative Example 17

A commercial sample of nickel chromite ($NiCr_2O_4$, CAS Reg. No. [14721-18-7], 45.0 g, 22 mL, −12 to +20 mesh, (1.68 to 0.84 mm)) was pelletized, sieved, and placed in a ⅝" (1.58 cm) diameter Inconel™ nickel alloy reactor tube heated in a fluidized sand bath. The nickel chromite was purged with nitrogen and fluorinated following the general procedure. Hydrogen fluoride, CFC-1213xa, and chlorine vapor were co-fed to the reactor with a contact time of 30 seconds. The GC-MS analysis of the reactor effluent at 375° C. with a molar feed ratio of 20:1:4 is given in Table 2.

TABLE 2

Chlorofluorination of CFC-1213xa

| Ex. No. | HF/1213/Cl₂ Ratio | Temp ° C. | Reaction Products, GC Area Percent | | | | | | |
|---|---|---|---|---|---|---|---|---|---|
| | | | 1215xc | 217ba | 226da | 216aa | 216ba | 215aa | 215bb |
| C1 | 20/1/4 | 300 | 0.6 | 11.1 | 2.4 | 19.8 | 21.6 | 42.7 | 0 |
| C1 | 20/1/4 | 375 | 0.04 | 25.2 | 0.2 | 53.0 | 17.2 | 3.0 | 0 |
| C1 | 30/1/2 | 375 | 0.04 | 40.9 | 0.2 | 40.7 | 15.3 | 0.9 | 0 |
| C1 | 30/1/2 | 400 | 0.03 | 24.1 | 0.03 | 67.4 | 6.4 | 0.2 | 0 |
| 2 | 20/1/4 | 300 | 0.3 | 14.3 | 2.3 | 16.9 | 16.2 | 48.5 | 0 |
| 2 | 20/1/4 | 350 | 0.08 | 27.0 | 0.9 | 16.9 | 34.4 | 18.0 | 17.5 |
| 2 | 30/1/2 | 350 | 0.06 | 41.6 | 2.0 | 32.2 | 14.0 | 7.7 | 0 |
| 2 | 30/1/2 | 400 | 0 | 47.4 | 0.03 | 40.8 | 8.9 | 0.1 | 0 |
| 3 | 20/1/4 | 300 | 0.6 | 9.7 | 2.5 | 17.1 | 15.3 | 53.3 | 0 |
| 3 | 20/1/4 | 350 | 0.4 | 20.6 | 1.1 | 37.1 | 20.7 | 18.6 | 0.03 |
| 3 | 30/1/2 | 350 | 0.1 | 37.4 | 1.5 | 37.9 | 15.4 | 4.6 | 0 |
| 3ᵉ | 30/1/2 | 350 | 0.2 | 24.7 | 2.5 | 45.4 | 14.6 | 11.0 | 0 |
| 3 | 20/1/4 | 400 | 0.03 | 17.2 | 0.02 | 71.5 | 9.0 | 0.7 | 0 |
| 3 | 30/1/2 | 400 | 0.06 | 46.6 | 0.02 | 46.4 | 4.9 | 0.03 | 0 |
| 4 | 20/1/4ᵉ | 300 | 0.3 | 8.8 | 0.4 | 16.1 | 5.2 | 20.5 | 30.5 |
| 4 | 20/1/4 | 400 | 0.09 | 14.8 | 0.1 | 26.6 | 34.9 | 17.5 | 1.6 |
| 5 | 20/1/4ʲ | 300 | 0.3 | 7.0 | 0.8 | 20.6 | 5.9 | 31.1 | 24.7 |
| 5 | 20/1/4 | 350 | 0.1 | 15.5 | 0.54 | 25.2 | 30.8 | 18.2 | 5.3 |
| 5 | 30/1/2 | 350 | 0.2 | 22.6 | 0.8 | 26.8 | 28.6 | 10.1 | 5.9 |
| 5 | 20/1/4 | 400 | 0.09 | 13.7 | 0.3 | 32.4 | 31.6 | 18.1 | 0 |
| 5 | 30/1/2 | 400 | 0.1 | 21.6 | 0.5 | 33.5 | 30.1 | 9.9 | 0.03 |
| 6 | 20/1/4 | 300 | 0.6 | 11.1 | 1.3 | 18.7 | 18.4 | 44.8 | 2.6 |
| 6 | 20/1/4 | 350 | 0.1 | 20.5 | 0.7 | 29.1 | 27.0 | 21.0 | 0 |
| 6 | 30/1/2 | 350 | 0.2 | 32.6 | 1.3 | 29.9 | 24.7 | 9.5 | 0 |
| 6 | 30/1/2 | 400 | 0.04 | 36.7 | 0.2 | 36.6 | 21.7 | 2.6 | 0 |
| 7 | 20/1/4 | 300 | 0.3 | 8.4 | 3.1 | 10.0 | 9.0 | 60.4 | 7.1 |
| 7 | 20/1/4 | 350 | 0.2 | 21.0 | 1.8 | 19.6 | 24.7 | 29.6 | 0.05 |
| 7 | 30/1/4 | 350 | 0.2 | 24.3 | 1.2 | 20.7 | 24.0 | 25.7 | 0.3 |
| 7 | 20/1/4 | 400 | 0.08 | 20.8 | 0.4 | 28.4 | 25.6 | 21.4 | 0 |
| 7 | 30/1/2 | 400 | 0.1 | 31.7 | 1.1 | 33.7 | 19.6 | 10.6 | 0 |

TABLE 2-continued

Chlorofluorination of CFC-1213xa

| Ex. No. | HF/1213/Cl$_2$ Ratio | Temp ° C. | Reaction Products, GC Area Percent | | | | | | |
|---|---|---|---|---|---|---|---|---|---|
| | | | 1215xc | 217ba | 226da | 216aa | 216ba | 215aa | 215bb |
| 8 | 20/1/4 | 300 | 0.9 | 11.3 | 2.0 | 18.5 | 13.9 | 50.7 | 1.1 |
| 8 | 20/1/4 | 350 | 0.3 | 19.7 | 1.0 | 32.5 | 21.2 | 23.1 | 0 |
| 8 | 30/1/2 | 350 | 0.2 | 37.5 | 1.7 | 29.7 | 19.3 | 8.8 | 0 |
| 9 | 20/1/4 | 300 | 0.7 | 9.5 | 0.8 | 13.3 | 24.3 | 42.8 | 6.2 |
| 9 | 20/1/4 | 350 | 0.3 | 9.8 | 0.4 | 35.3 | 26.6 | 25.8 | 0 |
| 9 | 20/1/4 | 400 | 0.07 | 13.1 | 0.06 | 58.2 | 20.1 | 6.5 | 0.1 |
| 10 | 20/1/4 | 300 | 1.6 | 11.4 | 2.0 | 17.4 | 15. | 50.6 | 0.1 |
| 10 | 20/1/4 | 350 | 0.4 | 20.4 | 0.9 | 34.1 | 18.6 | 23.8 | 0 |
| 10 | 30/1/2 | 350 | 0.4 | 27.6 | 3.0 | 42.9 | 12.2 | 12.0 | 0 |
| 11[f] | 20/1/4 | 350 | 0.2 | 10.9 | 0.3 | 23.3 | 15.6 | 21.2 | 23.9 |
| 11[b,c] | 20/1/4 | 350 | 0.7 | 3.3 | 0.5 | 32.1 | 23.3 | 35.7 | 1.0 |
| 12[g] | 20/1/4 | 300 | 0.4 | 3.6 | 1.6 | 18.4 | 4.8 | 55.6 | 10.7 |
| 12 | 20/1/4 | 350 | 0.3 | 9.9 | 1.1 | 29.7 | 17.4 | 32.6 | 5.9 |
| 13 | 20/1/4 | 300 | 2.2 | 8.5 | 3.1 | 21.6 | 17.0 | 46.3 | 0 |
| 13 | 20/1/4 | 350 | 0.2 | 15.8 | 0.7 | 55.6 | 15.3 | 11.1 | 0.09 |
| 13 | 30/1/2 | 375 | 0.2 | 27.4 | 0.2 | 58.9 | 10.4 | 1.0 | 0.02 |
| 14 | 20/1/4 | 300 | 1.6 | 9.2 | 2.4 | 17.1 | 22.0 | 44.3 | 1.8 |
| 14 | 20/1/4 | 350 | 0.4 | 18.1 | 1.3 | 30.1 | 25.1 | 22.9 | 0.2 |
| 14 | 30/1/2 | 400 | 0.1 | 31.1 | 0.3 | 41.2 | 20.6 | 4.6 | 0.06 |
| 15 | 20/1/4 | 300 | 0.8 | 12.5 | 1.9 | 16.0 | 18.6 | 46.3 | 1.8 |
| 15 | 20/1/4 | 350 | 0.2 | 19.4 | 1.2 | 35.5 | 18.6 | 23.0 | 0 |
| 15 | 30/1/2 | 375 | 0.2 | 34.0 | 1.0 | 40.8 | 16.3 | 5.0 | 0 |
| C16[d,h] | 30/1/2 | 375 | 2.1 | 0.3 | 0 | 0.8 | 0.5 | 9.7 | 26.0 |
| C17[b,i] | 20/1/4 | 375 | 1.5 | 0 | 0.5 | 1.6 | 6.9 | 45.5 | 8.8 |

[a]Other products formed include 13, 112, 113, 114, 114a, 115, 216cb, 217ca, 218, 225da, 1214, 1225, and 214ab.
[b]Contact time = 30 seconds.
[c]Different catalyst sample prepared by the same procedure.
[d]Products include 13.2% CFC-1214's.
[e]Products included 14.1% CFC-214ab and 0.1% unconverted CFC-1213xa.
[f]Products included 0.4% CFC-214ab.
[g]Products included 2.7% CFC-214ab.
[h]Products included 18.8% CFC-214ab and 27.1% unconverted CFC-1213xa.
[i]Products included 3.1% CFC-214ab and 24.9% unconverted CFC-1213xa.
[j]Products included 6.6% unconverted CFC-1213xa.

What is claimed is:

1. A process for the preparation of 2-chloro-1,1,1,2,3,3,3-heptafluoropropane, comprising:
   (a) contacting a mixture comprising hydrogen fluoride, chlorine, and at least one starting material selected from the group consisting of halopropenes of the formula $CX_3CCl=CX_2$ and halopropanes of the formula $CX_3CClYCX_3$, wherein each X is independently selected from the group consisting of F and Cl, and Y is selected from the group consisting of H, Cl and F, provided that the number of X and Y which are F totals no more than six, with a chlorofluorination catalyst in a reaction zone to produce a product mixture comprising $CF_3CClFCF_3$, HCl, HF, and underfluorinated halogenated hydrocarbon intermediates;
wherein said chlorofluorination catalyst comprises at least one chromium-containing component selected from (i) a crystalline alpha-chromium oxide where at least 0.05 atom % of the chromium atoms in the alpha-chromium oxide lattice are replaced by nickel, trivalent cobalt or both nickel and trivalent cobalt, provided that no more than 2 atom % of the chromium atoms in the alpha-chromium oxide lattice are replaced by nickel and that the total amount of chromium atoms in the alpha-chromium oxide lattice that are replaced by nickel and trivalent cobalt is no more than 6 atom %, and (ii) a fluorinated crystalline oxide of (i).

2. The process of claim 1 further comprising
   (b) separating the product of step (a) to recover $CF_3CClFCF_3$ as a product and to obtain underfluorinated halogenated hydrocarbon intermediates; and
   (c) returning underfluorinated halogenated hydrocarbon intermediates obtained in step (b) back to the step (a) reaction zone.

3. A process for the manufacture of a mixture of $CF_3CHFCF_3$ and $CF_2=CFCF_3$ by reacting a starting mixture comprising $CF_3CClFCF_3$ and hydrogen in the vapor phase at an elevated temperature, optionally in the presence of a hydrogenation catalyst, characterized by preparing the $CF_3CClFCF_3$ by the process of claim 1.

* * * * *